United States Patent [19]

Wong

[11] 4,384,869
[45] May 24, 1983

[54] ACTIVATION OF HYPOCHLORITE BLEACHING OF DYES

[75] Inventor: Louis F. Wong, Fairfield, Ohio

[73] Assignee: The Procter & Gamble Company, Cincinnati, Ohio

[21] Appl. No.: 333,952

[22] Filed: Dec. 23, 1981

Related U.S. Application Data

[62] Division of Ser. No. 204,120, Nov. 5, 1980, Pat. No. 4,353,866.

[51] Int. Cl.³ .................... C09B 67/24; C09B 11/12; D06P 1/673
[52] U.S. Cl. .................................. 8/527; 8/462; 8/620; 8/657; 8/658
[58] Field of Search ................ 8/462, 527, 620, 606, 8/657, 658

[56] References Cited

U.S. PATENT DOCUMENTS

| | | | |
|---|---|---|---|
| 2,987,435 | 6/1961 | Davies et al. | 167/18 |
| 3,120,424 | 2/1964 | Ruedi | 8/108 |
| 3,156,521 | 11/1964 | Mills | 8/108 |
| 3,504,384 | 4/1970 | Radley et al. | 4/228 |
| 3,547,573 | 12/1970 | Tourdot et al. | 8/108 |
| 3,700,401 | 10/1972 | Spangler | 8/108 |
| 3,770,371 | 11/1973 | Bossard et al. | 8/620 |
| 4,200,606 | 4/1980 | Kitko | 422/37 |
| 4,248,827 | 2/1981 | Kitko | 422/37 |

FOREIGN PATENT DOCUMENTS

| | | |
|---|---|---|
| 3918758 | 7/1958 | Australia . |
| 280178 | 2/1968 | Australia . |
| 557828 | 9/1956 | Belgium . |
| 562976 | 12/1956 | Belgium . |
| 519002 | 11/1955 | Canada . |
| 596192 | 1/1948 | United Kingdom . |
| 596193 | 1/1948 | United Kingdom . |
| 1137474 | 12/1968 | United Kingdom . |
| 1071494 | 6/1976 | United Kingdom . |
| 2007657 | 5/1979 | United Kingdom . |

*Primary Examiner*—Maria Parrish Tungol
*Attorney, Agent, or Firm*—Richard C. Witte; Ronald L. Hemingway

[57] ABSTRACT

A method of bleaching of certain triarylmethane dyes in aqueous systems with low concentration of hypochlorite ion, activated by the presence of bromide ion and ammonium ions. The method is particularly useful in providing a disappearing color signal in the automatic cleaning and sanitizing of toilet bowls with low concentrations of hypochlorite. Compositions and articles for implementing the practice of the method in the automatic cleaning and sanitizing of toilet bowls are also disclosed.

8 Claims, No Drawings

ACTIVATION OF HYPOCHLORITE BLEACHING OF DYES

This is a division of application Ser. No. 204,120 filed Nov. 5, 1980, now U.S. Pat. No. 4,353,866.

TECHNICAL FIELD

The present invention relates to the activation of the bleaching of certain triarylmethane dyes with low concentrations of hypochlorite, wherein the activator is a combination of ammonium ion and bromide ion. The invention is particularly useful in the automatic cleaning and sanitizing of flush toilets. The dye and a hypochlorite sanitizing agent are separately and simultaneously dispensed to the toilet bowl (with activator) with each flush. The dye is bleached by the hypochlorite to a colorless state in the toilet bowl within a short time after flushing, thereby providing a visual signal of the activity of the hypochlorite.

BACKGROUND ART

This invention relates to the bleaching of certain triarylmethane dyes in solution with low concentrations of hypochlorite ion, activated by the combination of bromide ion and ammonium ion. In particularly preferred embodiments, the invention relates to methods, compositions and articles for automatically cleaning and sanitizing toilets wherein a dye/activator composition and hypochlorite are separately dispensed into the toilet bowl during flushing. The water in the bowl at the end of the flush is colored by the dye. However, within a relatively short period of time after the flush, the dye is oxidized to a colorless state thereby providing a visual signal that the hypochlorite sanitizing agent is present and "acting" in the bowl.

Automatically dispensed toilet bowl cleaning and/or sanitizing products, which contain dyes to provide a visual signal to the user that product is being dispensed, are well known. Such products are sold in the United States under the brand names VANISH AUTOMATIC (Drackett Products), TY-D-BOL AUTOMATIC (Knomark, Inc.) and SANIFLUSH AUTOMATIC (Boyle-Midway). None of these products contains a hypochlorite sanitizing agent and all of them provide a color to the bowl water which persists between flushing. U.S. Pat. No. 3,504,384, Radley et al., issued Apr. 7, 1970, discloses a dual compartment dispenser for automatically dispensing a hypochlorite solution and a surfactant/dye solution to the toilet bowl during flushing. The dye which is taught in the patent is Disulfide Blue VN150. It is believed that the dye referred to in Radley et al. is actually Disulphine Blue VN150 (Color Index No. 42045). (The abbreviation "C.I." will be used hereinafter to designate "Color Index.") This dye has been reported in U.S. Ser. No. 915,027, Kitko, filed June 12, 1978 to be quite resistant to oxidation to a colorless state by hypochlorite; thus, it too provides a persistent color to the toilet bowl water, even in the presence of the hypochlorite.

A persistent color in the toilet bowl water has certain attendant negatives. The dye can cause staining of the toilet bowl itself or of deposits (such as water hardness deposits) which accumulate on the surfaces of the bowl between manual cleanings. Also, a persistent colored solution in the bowl will tend to obscure medical symptoms such as the passing of blood during excretion or urination. Further, a persistent color in the toilet bowl water tends to obscure otherwise visible evidence of soiling on surfaces of the toilet bowl which are below the water line.

U.S. Ser. No. 915,027 supra discloses certain dyes which are bleached to a colorless state in less than 10 minutes in the toilet bowl by low concentrations of hypochlorite or hypochlorite which is catalyzed by bromide ion. Among these is the triarylmethane dye Acid Green 2G (C.I. No. 42085). In this dye there are no substituents on the aryl rings in the positions which are ortho to the ring carbon which is attached to the methane carbon. U.S. Ser. No. 915,027 also discloses certain triarylmethane dyes which are not bleached to a colorless state within the stated 10 minute period by hypochlorite or hypochlorite/bromide. These are FD&C Blue No. 1 (C.I. No. 42090), FD&C Green No. 3 (C.I. No. 42053) and Disulphine Blue VN (C.I. No. 42045). All of these triarylmethane dyes have a substituent group in the ortho position on one of the aryl rings attached to the methane carbon.

An object of the present invention is to provide a method for bleaching aqueous solutions of triarylmethane dyes which have a substituent in the ortho position of at least one of the aryl rings attached to the methane carbon, with low concentrations of hypochlorite ion.

Another object of the invention is to provide a method for automatic cleaning and sanitization of toilets wherein a visual color signal is provided to indicate that the sanitizing agent is present and acting in the toilet bowl, and to provide articles and compositions adapted for use in the said method.

Another object of the invention is to provide a visual color signal which persists in the toilt bowl for a relatively short time after flushing.

Another object of the invention is to provide, by a visual color signal, a means by which the consumer will know when a new supply of sanitizing agent needs to by provided for the toilet.

DISCLOSURE OF THE INVENTION

The present invention broadly relates to a method of bleaching water-soluble triarylmethane dyes which have in their structure the moiety

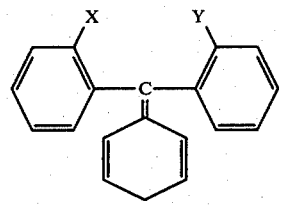

wherein X is selected from the group consisting of substituent groups other than hydrogen or methyl and Y is selected from the group consisting of X, hydrogen and methyl, said method comprising the step of forming a solution comprising from about 0.02 to about 2 ppm of said dye, from about 2 to about 30 ppm of available chlorine from hypochlorite ion, from about 0.1 to about 3 ppm bromide ion and from about 0.1 to about 2 ppm ammonium ion, the available chlorine to dye ratio in said solution being from about 2:1 to about 150:1, and the pH of said solution being from about 6 to about 9.5. (All compositions, concentrations and proportions herein are stated on a "by weight" basis unless indicated otherwise).

In a preferred aspect, the present invention relates to a method of treating a flush toilet, which comprises a flush tank and bowl, with a hypochlorite sanitizing agent each time the toilet is flushed, and providing a transitory visual signal to indicate the activity of the sanitizing agent in the bowl. The said method comprises the step of dispensing from separate dispensing means, into the flush water; (A) an aqueous solution of a compound which produces hypochlorite ion in aqueous solution; and (B) an aqueous solution comprising a triarylmethane dye as described above, a compound which produces bromide ion in aqueous solution and a compound which produces ammonium ion in aqueous solution, thereby to form a solution in the toilet bowl at the end of the flush cycle which comprises from about 0.02 to about 2 ppm of said dye, from about 2 ppm to about 30 ppm available chlorine from said hypochlorite ion, from about 0.1 ppm to about 3 ppm bromide ion, from about 0.1 ppm to about 2 ppm ammonium ion and an available chlorine to dye ratio of from about 2:1 to about 150:1, said solution in said bowl having a pH of from about 6 to about 9.5, wherein said solution in said bowl is bleached from a colored state to a colorless state within about 40 minutes (preferably within about 20 minutes) after the end of said flush cycle.

The bromide and ammonium ions function as "activators" which accelerate the bleaching action of the hypochlorite on the dye.

The invention also comprises articles of manufacture and compositions useful in carrying out the method in a flush toilet.

Since the preferred aspect of the present invention relates to its use in the automatic cleaning and sanitizing of flush toilets, the invention will be described herein primarily in the context of that utility.

The term "water-soluble" as used herein means that the material in question has a solubility in ambient temperature water which is sufficient to produce the concentrations specified for that material in the hereindescribed invention.

THE SANITIZING AGENT

The sanitizing agent of the present invention can by any compound which provides the hypochlorite ion (OCl⁻) in aqueous solution. Such compounds include alkali metal and alkaline earth metal hypochlorites, hypochlorite addition products, chloramines, chlorimines, chloramides, and chlorimides. Specific examples of compounds of this type include sodium hypochlorite, potassium hypochlorite, lithium hypochlorite, calcium hypochlorite, calcium hypochlorite dihydrate, monobasic calcium hypochlorite, dibasic magnesium hypochlorite, chlorinated trisodium phosphate dodecahydrate, potassium dichloroisocyanurate, sodium dichloroisocyanurate, sodium dichloroisocyanurate dihydrate, 1,3-dichloro-5,5-dimethylhydantoin, N-chlorosulfamide, Chloramine T, Dichloramine T, Chloramine B, Dichloramine B, and Di-Halo (bromochlorodimethyl hydantoin). A particularly preferred sanitizing agent composition suitable for use in the practice of the present invention is described in the commonly assigned U.S. patent application of John D. Nyquist et al. entitled PASSIVE DOSING DISPENSER WITH IMPROVED HYPOCHLORITE CAKE, Ser. No. 019,547, filed Mar. 12, 1979, and the commonly assigned U.S. patent application of David J. Kitko entitled METHOD FOR SANITIZING TOILETS, Ser. No. 972,318, filed Dec. 22, 1978, both of said patent applications being incorporated herein by reference. The compositions described in said applications are compacted cakes comprising lithium hypochlorite and calcium hypochlorite. The composition in the Nyquist et al. application additionally comprises sodium metasilicate.

By virtue of the strong oxidizing power of the hypochlorite ion, it is highly effective in bleaching stains, breaking down and removing soils and killing microoganisms, thereby providing effective sanitizing action in the toilet bowl.

The amount of hypochlorite-providing sanitizing compound dispensed to the toilet in the process of the invention can vary over a wide range, but preferably should be sufficient to provide from about 2 to about 30 ppm (preferably from about 3 to about 8 ppm) available chlorine in the bowl water at the end of the flush. Only a very small amount of the available chlorine which is delivered to the bowl will be utilized in decolorizing the dye. The sanitizing agent can be formulated as an aqueous liquid if it is to be dispensed from a dispensing means designed to receive liquids. The sanitizing agent can also be formulated into the form of a solid cake for use in dispensing means which are designed to receive a cake of solid material (see description of dispensing means below). The level of available chlorine in the bowl water can be measured by well-known methods such as the DPD Ferrous Titrametric Method or the Stabilized Neutral Orthotolidine Method, described, respectively, at pages 129 and 126 of Standard Methods for the Examination of Water and Wastewater, 13th Ed., published by American Public Health Association.

DYES

The dyes of the present invention are watersoluble triarylmethane dyes which have in their formula the structural feature

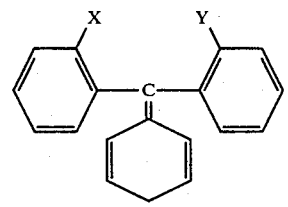

wherein X is a substituent other than hydrogen or methyl, and Y is a substituent selected from X, hydrogen and methyl. Y is preferably hydrogen. The X substituent can be any of a wide variety of substituent groups. These include alkyls such as isopropyl, and tertiary butyl, halogens such as chlorine or bromine, sulfonate, phosphate, carboxylate, hydroxyl and the like. For purposes of convenient description, these dyes will be referred to herein as ortho-substituted triarylmethane dyes since they all contain a substituent on at least one of the aryl rings in a position ortho to the carbon attached to the methane carbon.

Examples of particular commercially available dyes which can be used in the present invention are FD&C Green No. 3 (C.I. No. 42053), FD&C Blue No. 1 (C.I. No. 42090), Acid Green No. 9 (C.I. No. 42100) and Hidacid Blue V Conc., which is the same structure as Disulphine Blue VN, both being designated by C.I. No. 42045. Preferred dyes herein are C.I. Nos. 42053, 42090 and 42100.

The molecular structures of these dyes are as follows:

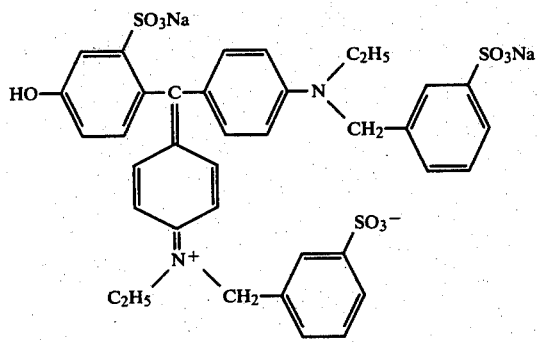

FD&C Green No. 3 (C.I. 42053)

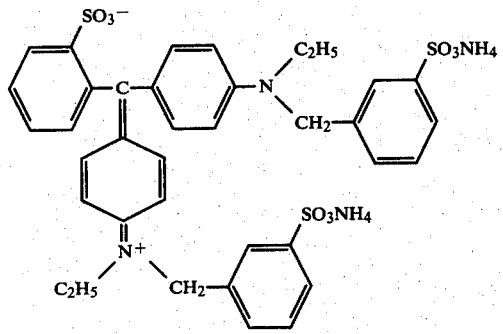

FD&C Blue No. 1 (C.I. 42090)

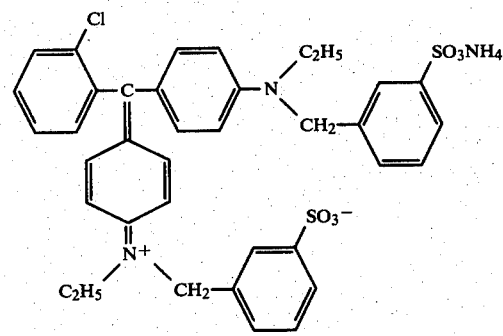

Acid Green No. 9 (C.I. 42100)

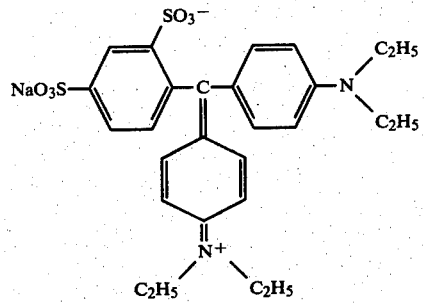

Hidacid Blue V Conc. (C.I. 42045)

When used to provide a colored-to-colorless color change signal in the automatic cleaning and sanitizing of toilets in accordance with the invention herein, the amount of dye dispensed to the toilet will depend on the color intensity desired, the amount of hypochlorite sanitizing agent dispensed into the toilet with the dye, and on the quickness with which it is desired to have the color disappear. Generally, the amount of dye dispensed will be sufficient to produce a dye concentration of from about 0.02 to about 2 ppm, preferably from about 0.15 ppm to about 1.0 ppm in the toilet bowl. Generally, the dye should be present in a ratio of available chlorine:dye of from 2:1 to about 150:1, preferably from about 5:1 to about 60:1. Dye concentrations and ratios herein are based upon the amount of the actual dye compound, unless specified otherwise. Dyes are normally sold in the form of mixtures of dye compound and inert diluent. For example, FD&C Blue No. 1, FD&C Green No. 3, Acid Green No. 9 and Hidacid Blue V Conc. are believed to be about 90% actual dye.

The following test data show the effect of the presence of ammonium ion, bromide ion and the combination of ammonium ion and bromide ion in the bleaching of dyes of the present invention with hypochlorite. The test was conducted according to the following procedure at pH 6.5, 8 and 9, since this represents the typical range of pH's found in tap water.

One liter of distilled water at 70° F. is placed in a two liter beaker, and the water is kept in stirring motion with a magnetic stirrer. The appropriate amount of sodium hypochlorite is added via a pipette to the water from a 0.5% available chlorine aqueous stock solution of sodium hypochlorite, so as to yield 5 ppm available chlorine in the test solution. The pH is then adjusted to the desired level with a 1% aqueous solution of NaOH or HCl, as needed. The appropriate amounts of sodium bromide and ammonium chloride are added from 0.1% aqueous stock solutions to provide the desired concentrations of these ions. The color change reaction is initiated by the addition of the appropriate amount of a stock solution of dye (0.1% dye, on an "as received" basis, in water). The solution is then observed to determine the time for disappearance of color.

The following tables present data on the testing of the four above-mentioned commercially available orthosubstituted triarylmethane dyes at a hypochlorite concentration of 5 ppm available chlorine. The absolute time values obtained in these discoloration tests are not necessarily the same as will be experienced in actual dispensing of dye/activator solution and hypochlorite solution into the toilet via the flush tank during flushing. Generally, the time values obtained in such actual use situations are somewhat shorter. This is due to the fact that when the respective concentrated solutions are dispensed into the flush water during the flush they come into contact with each other before being completely diluted to the concentration desired in the bowl. Contact between the hypochlorite, dye and activator ions before dilution to the intended bowl water concentration results in a faster reaction rate during the short period in which such contact occurs. Nevertheless, the data in Tables 1–4 are consistent in demonstrating the enhanced bleaching effect obtained by combining ammonium and bromide ions as activators for bleaching of the subject dyes.

TABLE 1

| FD&C Blue No. 1 (0.45 ppm*) | | | |
| --- | --- | --- | --- |
| pH | ppm Br$^-$ | ppm NH$_4^+$ | Time for Color Disappearance (Minutes) |
| 6.5 | 0 | 0 | >60 |

TABLE 1-continued

FD&C Blue No. 1 (0.45 ppm*)

| pH | ppm Br⁻ | ppm NH₄⁺ | Time for Color Disappearance (Minutes) |
|---|---|---|---|
| 6.5 | 1 | 0 | >60 |
| 6.5 | 0 | 0.225 | 22 |
| 6.5 | 1 | 0.225 | 10 |
| 8 | 0 | 0 | >60 |
| 8 | 1 | 0 | 38 |
| 8 | 0 | 0.225 | 25 |
| 8 | 1 | 0.225 | 14 |
| 9 | 0 | 0 | >60 |
| 9 | 1 | 0 | >60 |
| 9 | 0 | 0.225 | >60 |
| 9 | 1 | 0.225 | 25 |

*0.5 ppm on "as received" basis

TABLE 2

FD&C Green No. 3 (0.45 ppm*)

| pH | ppm Br⁻ | ppm NH₄⁺ | Time for Color Disappearance (Minutes) |
|---|---|---|---|
| 6.5 | 0 | 0 | >60 |
| 6.5 | 1 | 0 | 20 |
| 6.5 | 0 | 0.225 | 40 |
| 6.5 | 1 | 0.225 | 10 |
| 8 | 0 | 0 | >60 |
| 8 | 1 | 0 | 28 |
| 8 | 0 | 0.225 | 30 |
| 8 | 1 | 0.225 | 4 |
| 9 | 0 | 0 | >60 |
| 9 | 1 | 0 | >60 |
| 9 | 0 | 0.225 | >60 |
| 9 | 1 | 0.225 | 30 |

*0.5 ppm on "as received" basis

TABLE 3

Acid Green 9 (0.9 ppm*)

| pH | ppm Br⁻ | ppm NH₄⁻ | Time for Color Disappearance (Minutes) |
|---|---|---|---|
| 6.5 | 0 | 0 | >60 |
| 6.5 | 1 | 0 | 21 |
| 6.5 | 0 | 0.225 | >60 |
| 6.5 | 1 | 0.225 | 15 |
| 8 | 0 | 0 | >60 |
| 8 | 1 | 0 | 29 |
| 8 | 0 | 0.225 | >60 |
| 8 | 1 | 0.225 | 12 |
| 9 | 0 | 0 | 35 |
| 9 | 1 | 0 | 37 |
| 9 | 0 | 0.225 | 30 |
| 9 | 1 | 0.225 | 19 |

*1 ppm on "as received" basis

TABLE 4

Hidacid Blue V Conc. (0.45 ppm*)

| pH | ppm Br⁻ | ppm NH₄⁺ | Time for Color Disappearance (Minutes) |
|---|---|---|---|
| 6.5 | 0 | 0 | 15 |
| 6.5 | 1 | 0 | >60 |
| 6.5 | 0 | 0.225 | 20 |
| 6.5 | 1 | 0.225 | 7 |
| 8 | 0 | 0 | >60 |
| 8 | 1 | 0 | 8 |
| 8 | 0 | 0.225 | 20 |
| 8 | 1 | 0.225 | 4 |
| 9 | 0 | 0 | >60 |
| 9 | 1 | 0 | 35 |
| 9 | 0 | 0.225 | >60 |
| 9 | 1 | 0.225 | 21 |

*0.5 ppm on "as received" basis

While not wishing to be bound by theory, it is believed that the ortho-substituted triarylmethane dyes herein are resistant to bleaching by hypochlorite because of the steric and/or electrostatic effects of the substituents in the ortho position. It is believed that the activator ions react with hypochlorite to form species which attack the dye at sites different from those at which hypochlorite attacks. More specifically, it is believed that with the activator species, the attack occurs at double bond sites (electrophilic addition), rather than at the triarylmethane carbon (nucleophilic addition).

ACTIVATOR IONS

The activator system for carrying out the method of the present invention is the combination of ammonium ions and bromide ions. These ions can be supplied by any water-soluble source of the ions. For example, bromide ion can be provided by water-soluble inorganic salts such as the alkali metal bromides (e.g., sodium and potassium bromides), alkaline earth metal bromides (e.g., calcium and magnesium bromides), zinc bromide and ferric bromide. Organic salts such as cetylpyridinium bromide and cetyltrimethylammonium bromide can also be used. In the context of toilet bowl treatment, the alkali metal bromides and ammonium bromide are preferred. Ammonium ions can be provided by inorganic salts such as ammonium chloride, ammonium sulfate, ammonium nitrate, ammonium phosphate and ammonium fluoride, or organic salts such as ammonium formate, ammonium citrate or ammonium acetate.

A preferred source of both ammonium and bromide ions is ammonium bromide.

The amount of ammonium ion and bromide ion, respectively, which should be present in solution to activate the bleaching of the ortho-substituted triarylmethane dyes in the method of the invention can vary over a wide range. Generally there should be at least about 0.1 ppm of each ion. Preferably there should be from about 0.1 to about 3 ppm bromide ion and 0.1 to 2 ppm ammonium ion, and most preferably from about 0.2 to about 1 ppm of each ion.

When formulated into compositions suitable for use in the method herein to separately provide hypochlorite and dye to the toilet bowl, the compounds which provide the ammonium and bromide activator ions should be formulated into the dye composition, rather than the hypochorite sanitizer composition.

DYE/ACTIVATOR-SALT COMPOSITIONS

The dyes and activator salts herein can be formulated into compositions for use in the method herein. Such compositions will normally comprise from about 0.2% to about 15% dye and an amount of activator salts sufficient to provide from about 0.5% to about 18% (preferably from about 2% to about 8%) bromide ion and from about 0.5% to about 11% (preferably from about 0.5% to about 1.5%) ammonium ion in the composition.

Optionally, these dye-activator-salt compositions can contain other ingredients which it is desired to dispense into the toilet bowl, such as, for example, surfactants, sequestering agents and perfumes, as well as diluents such as water, organic solvents such as ethanol, and organic or inorganic salts such as sodium sulfate, sodium chloride and sodium acetate.

Surfactants can provide enhanced cleaning performance through breakup and emulsification of soils, and also provide some sudsing in the toilet bowl, which may be aesthetically desirable. Perfumes provide a pleasant smell to the area surrounding the toilet and also help to obscure the "bleach" smell of the sanitizing agent. Sequestrants aid soil removal by sequestration of multivalent metal ions.

When the dyes and activator-salts herein are formulated with surfactants, the resulting compositions will generally comprise from about 5% to about 95% surfactant. Perfumes will normally be used at levels of up to about 25% and inert diluents at levels up to about 90%. Sequestering agents such as potassium pyrophosphate, sodium tripolyphosphate and ethylenediamine pentaacetate can be used at levels up to about 25%.

Certain particularly desirable sequestering agents which prevent the formation of stains on toilet bowl surfaces caused by hypochlorite-oxidation of manganese ions which may be present in the water supply are the partially hydrolyzed polyacrylate polymers and ethylene-maleic anhydride polymers described in copending, commonly assigned applications of Robert H. Callicott, U.S. Ser. No. 028,293, filed Apr. 9, 1979; Robert H. Callicott, U.S. Ser. No. 028,613, filed Apr. 9, 1979; and James L. Kurtz, U.S. Ser. No. 028,612, filed Apr. 9, 1979, all incorporated herein by reference. Examples of suitable partially hydrolyzed polyacrylamide polymers which are commercially available are P-35 and P-70 from American Cyanamid Company and examples of suitable commercially available ethylene-maleic anhydride polymers are EMA-21 and EMA-31 from Monsanto Company.

Compositions comprising the dye, activator salts and a surfactant and/or other ingredients can be conveniently formed into a cake for use in dispensers which are designed to receive a cake of solid material (see description of dispensing means, below). Such cakes can be made by extrusion or hydraulic stamping, or by pouring a melt of the composition into a mold and solidifying the composition by cooling.

If it is desired to use a dispensing means which is designed to receive liquids, the dye, activator salts and any optional ingredients such as surfactants, etc., can be formulated into liquid compositions.

Surfactants suitable for use in the compositions herein can be of the anionic, nonionic, ampholytic or zwitterionic type.

Anionic surfactants operable in compositions suitable for use in practicing the present invention can be broadly described as the water-soluble salts, particularly the alkali metal salts, of organic sulfuric acid reaction products having in their molecular structure an alkyl or alkaryl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the anionic surfactants which can be employed in the practicing of the present invention are the sodium or potassium alkyl sulfates, especially those obtained by sulfating the higher alcohols ($C_8$–$C_{18}$ carbon atoms) produced by reducing the glycerides of tallow or coconut oil; sodium or potassium alkyl benzene sulfonates, in which the alkyl group contains from about 9 to about 15 carbon atoms, (the alkyl radical can be a straight or branched aliphatic chain); paraffin sulfonate surfactants having the general formula $RSO_3M$, wherein R is a primary or secondary alkyl group containing from about 8 to about 22 carbon atoms (preferably 10 to 18 carbon atoms) and M is an alkali metal, e.g., sodium or potassium; sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid esters of the reaction product of one mole of a higher fatty alcohol (e.g., tallow or coconut oil alcohols) and about 1 to 10 moles of ethylene oxide; sodium or potassium salts of alkyl phenol ethylene oxide ether sulfates with about 1 to about 10 units of ethylene oxide per molecule and in which the alkyl radicals contain from about 8 to about 12 carbon atoms; the reaction products of fatty acids esterified with isethionic acid and neutralized with sodium hydroxide where, for example, the fatty acids are derived from coconut oil; sodium or potassium salts of fatty acid amides of a methyl tauride in which the fatty acids, for example, are derived from coconut oil and sodium or potassium $\beta$-acetoxy- or $\beta$-acetamido-alkane-sulfonates where the alkane has from 8 to 22 carbon atoms.

Nonionic surfactants which can be used in practicing the present invention can be of three basic types—the alkylene oxide condensates, the amides and the semipolar nonionics.

The alkylene oxide condensates are broadly defined as compounds produced by the condensation of alkylene oxide groups (hydrophilic in nature) with an organic hydrophobic compound, which can be aliphatic or alkyl aromatic in nature. The length of the hydrophilic or polyoxyalkylene radical which is condensed with any particular hydrophobic group can be readily adjusted to yield a water-soluble-compound having the desired degree of balance between hydrophilic and hydrophobic elements.

Examples of such alkylene oxide condensates include:

1. The condensation products of aliphatic alcohols with ethylene oxide. The alkyl chain of the aliphatic alcohol can either be straight or branched and generally contains from about 8 to about 22 carbon atoms. Examples of such ethoxylated alcohols include the condensation product of about 6 moles of ethylene oxide with 1 mole of tridecanol, myristyl alcohol condensed with about 10 moles of ethylene oxide per mole of myristyl alcohol, the condensation product of ethylene oxide with coconut fatty alcohol wherein the coconut alcohol is a mixture of fatty alcohols with alkyl chains varying from 10 to 14 carbon atoms and wherein the condensate contains about 6 moles of ethylene oxide per mole of alcohol, and the condensation product of about 9 moles of ethylene oxide with the above-described coconut alcohol. Examples of commercially available nonionic surfactants of this type include Tergitol 15-S-9 marketed by the Union Carbide Corporation, Neodol 23-6.5 marketed by the Shell Chemical Company and Kyro EOB marketed by The Procter & Gamble Company.

2. The polyethylene oxide condensates of alkyl phenols. These compounds include the condensation products of alkyl phenols having an alkyl group containing from about 6 to about 12 carbon atoms in either a straight chain or branched chain configuration, with ethylene oxide, the said ethylene oxide being present in amounts equal to 5 to 25 moles of ethylene oxide per mole of alkyl phenol. The alkyl substituent in such compounds can be derived, for example, from polymerized propylene, diisobutylene, octene, or nonene. Examples of compounds of this type include nonyl phenol condensed with about 9.5 moles of ethylene oxide per mole of nonyl phenol, dodecyl phenol condensed with about 12 moles of ethylene oxide per mole of phenol, dinonyl phenol condensed with about 15 moles of ethylene oxide per mole of phenol, di-isooctylphenol condensed with about 15 moles of ethylene oxide per mole of phenol. Commercially available nonionic surfactants of this type include Igepal CO-610 marketed by the GAF Corporation; and Triton X-45, X-114, X-110 and X-102, all marketed by the Rohm and Haas Company.

3. The condensation products of ethylene oxide with a hydrophobic base formed by the condensation of propylene oxide with propylene glycol. The hydrophobic portion of these compounds has a molecular weight of from about 1500 to 1800 and of course exhibits water insolubility. The addition of polyoxyethylene moieties of this hydrophobic portion tends to increase the water-solubility of the molecule. Examples of compounds of this type include certain of the commercially available Pluronic surfactants marketed by the Wyandotte Chemicals Corporation.

4. The condensation products of ethylene oxide with the product resulting from the reaction of propylene oxide and ethylene diamine. The hydrophobic base of these products consists of the reaction product of ethylene diamine and excess propylene oxide, said base having a molecular weight of from about 2500 to about 3000. This base is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic compounds marketed by the Wyandotte Chemicals Corporation.

Examples of the amide type of nonionic surfactants include the ammonia, monoethanol and diethanol amides of fatty acids having an acyl moiety of from about 8 to about 18 carbon atoms. These acyl moieties are normally derived from naturally occurring glycerides, e.g., coconut oil, palm oil, soybean oil and tallow, but can be derived synthetically, e.g., by the oxidation of petroleum, or by hydrogenation of carbon monoxide by the Fischer-Tropsch process.

Examples of the semi-polar type of nonionic surfactants are the amine oxides, phosphine oxides and sulfoxides. These materials are described more fully in U.S. Pat. No. 3,819,528, Berry, issued June 25, 1974, and incorporated herein by reference.

Ampholytic surfactants which can be used in practicing the present invention can be broadly described as derivatives of aliphatic amines which contain a long chain of about 8 to about 18 carbon atoms and an anionic water-solubilizing group, e.g., carboxy, sulfo and sulfato. Examples of compounds falling within this devinition are sodium-3-dodecylamino-propionate, sodium-3-dodecylamino propane sulfonate, and dodecyl dimethylammonium hexanoate.

Zwitterionic surfactants which can be used in practicing the present invention are broadly described as internally-neutralized derivatives of aliphatic quaternary ammonium and phosphonium and tertiary sufonium compounds, in which the aliphatic radical can be straight chain or branched, and wherein one of the aliphatic substituents contains from about 8 to about 18 carbon atoms and one contains an anionic water-solubilizing group, e.g., carboxy, sulfo, sulfato, phosphato, or phosphono.

Bleach-stable (i.e., hypochlorite-stable) surfactants which are especially resistant to oxidation are the alkyl sulfates and paraffin sulfonates. Alkyl sulfates are the water-soluble salts of sulfated fatty alcohols containing from about 8 to about 18 carbon atoms in the alkyl group. Examples of suitable alcohols which can be employed in alkyl sulfate manufacture include decyl, lauryl, myristyl, palmityl and stearyl alcohols and the mixtures of fatty alcohols derived by reducing the glycerides of tallow and coconut oil.

Specific examples of alkyl sulfate salts which can be employed in the instant surfactant/dye compositions include sodium lauryl alkyl sulfate, sodium stearyl alkyl sulfate, sodium palmityl alkyl sulfate, sodium decyl sulfate, sodium myristyl alkyl sulfate, potassium lauryl alkyl sulfate, potassium stearyl alkyl sulfate, potassium decyl sulfate, potassium palmityl alkyl sulfate, potassium myristyl alkyl sulfate, sodium dodecyl sulfate, potassium dodecyl sulfate, potassium tallow alkyl sulfate, sodium tallow alkyl sulfate, sodium coconut alkyl sulfate potassium coconut alkyl sulfate and mixtures of these surfactants. Highly preferred alkyl sulfates are sodium coconut alkyl sulfate, potassium coconut alkyl sulfate, potassium lauryl alkyl sulfate and sodium lauryl alkyl sulfate.

Paraffin sulfonate surfactants have the general formula $RSO_3M$, wherein R is a primary or secondary alkyl group containing from about 8 to about 22 carbon atoms (preferably 10 to 18 carbon atoms) and M is an alkali metal, e.g., sodium or potassium. Paraffin sulfonate surfactants and methods for their preparation are well known in the art. They may be prepared, for example, by reaction of hydrocarbons with sulfur dioxide, oxygen and a sulfonation reaction initiator. Alternatively, they may be prepared by reacting an alkene and a sodium bisulfite under suitable radiation or catalysis, as disclosed in British Pat. No. 1,451,228 published Sept. 29, 1976, and hereby incorporated herein by reference. Paraffin sulfonate surfactants are commercially available, e.g., from Farbwerke Hoechst A.G.

Preferred paraffin sulfonates herein are secondary paraffin sulfonates. Examples of specific paraffin sulfonates herein are:
Sodium-1-decane sulfonate;
Potassium-2-decane sulfonate;
Lithium-1-dodecane sulfonate;
Sodium-6-tridecane sulfonate;
Sodium-2-tetradecane sulfonate;
Sodium-1-hexadecane sulfonate;
Sodium-4-octadecane sulfonate;
Sodium-3-octadecane sulfonate.

Normally, the paraffin sulfonates are available as mixtures of individual chain lengths and position isomers, and such mixtures are suitable for use herein.

Naphthalene sulfonate surfactants are also suitable for use in the compositions herein. These are described in detail in the commonly assigned application of Choy, U.S. Ser. No. 154,000, filed May 28, 1980, incorporated by reference herein. Exemplary naphthalene sulfonate surfactants are Petro BAF and Petro 22 from Petrochemicals Company, Inc.

Another optional ingredient which can be included in the dye/activator-salt compositions herein is an organic solubility control agent for the surfactant, if surfactant is used. Such agents are described in the copending, commonly assigned application of Mark L. Kacher, U.S. Ser. No. 030,976, filed Apr. 18, 1979, incorporated herein by reference. An exemplary solubility control agent is isobornyl acetate. Such agents can be present in the compositions herein at levels of from about 0.5% to about 20%.

Another optional ingredient which can be included in the dye/activator-salt compositions herein is a poly(ethylene oxide) resin such as described in the copending, commonly assigned application of Clement K. Choy and Robert A. Greene, U.S. Ser. No. 153,993, filed May 28, 1980, incorporated by reference herein. These resins reduce the aerosolization of water from the toilet bowl during flushing. An exemplary poly(ethylene oxide) resin is Polyox C from Union Carbide Company.

If needed, pH adjusting agents such as sodium carbonate, sodium silicate, oxalic acid, citric acid, etc., can be incorporated into the dye/activator-salt composition. Normally, however, such agents are not needed since the flush water will already be within the desired pH range.

DISPENSING MEANS

In order to provide automatic sanitizing of the toilet bowl in accordance with the present invention, it is essential that the hypochlorite sanitizing agent, the dye and the ammonium and bromide activator ions, in the form of relatively concentrated solutions, be dispensed into the flush water each time the toilet is flushed.

It is within the contemplation of the present invention that the concentrated solution of one of the components (i.e., either the dye/activator composition or the sanitizing agent composition) be dispensed into the flush tank during the refill after a flush (thereby forming a dilute solution of one composition in the flush water which is stored in the tank between flushes) and that the concentrated solution of the other composition be dispensed into this treated flush water during the "down-flush," i.e., during the time the flush water is flowing from the tank to the bowl during the next succeeding flush. Dispensing means which operate to dispense solutions into a toilet tank during the time it is refilling are described, for example, in U.S. Pat. Nos. 1,798,090, Lebegue, issued Mar. 24, 1931; 3,339,801, Hronas, issued Sept. 5, 1967; and 3,121,236, Yadro et al., issued Feb. 18, 1964.

It is preferred that both of the concentrated solutions be dispensed into the flush water on the down-flush, i.e., that they be dispensed into the flush water during the time the flush water is flowing from the tank into the bowl. In this preferred mode of operation, it is additionally preferred that the dispensing of the hypochlorite and dye plus activator ions should occur near the end of the flush in order to avoid wastage of dye and hypochlorite and to keep to a minimum the time of contact between dye, hypochlorite and activator ions before they enter the bowl. The respective dispensing means for the hypochlorite and dye/activator solutions should preferably be in positions relative to each other in the toilet tank so that these concentrated solutions will be diluted by flush water during the flush before they come into contact with each other, i.e., intimate mixture of streams of the two concentrated solutions in the flush tank should preferably be avoided.

Dispensing means for automatically dispensing solutions of chemicals into the flush water during the down-flush are well known to the art. U.S. Pat. No. 3,504,384, Radley et al., issued Apr. 7, 1970, discloses a dual dispenser for separately dispensing a detergent/dye solution and a hypochlorite solution into the flush water during the flush. Water from the flush tank flows into the respective dispenser chambers as the tank fills after a flush, where it comes into contact with a solid detergent/dye composition and a solid hypochlorite-producing composition in the respective chambers. During the interval between flushes, relatively concentrated solutions of the hypochlorite and detergent/dye compositions form in the respective chambers, and these solutions are discharged into the flush water on the next flush. It should be noted that the inlet and outlet ports of the dispenser chambers in the Radley et al. dual dispenser are not closed between flushings, and therefore there is opportunity for ingredients in the respective concentrated solutions in the chambers to diffuse into the tank water between flushes, whereby there is also opportunity for ingredients from one dispenser chamber to utimately find their way into the solution in the other dispenser chamber. The longer the time interval between flushes, the more likelihood there is that some portion of the contents of the two dispenser chambers will have an opportunity to come into contact with each other before they are dispensed into the flush water on the next flush. While dispensing devices of the type disclosed in Radley et al. can be used in the method of the present invention, they are not preferred. Because of the high reactivity between the dye and the activiated hypochlorite, the color intensity and duration of the color signal in the bowl will be less reproducible from one flush to the next than if the dye/activator composition and hypochlorite composition are substantially completely isolated from the tank water (and, therefore, from each other) between flushes. This isolation can be accomplished in the dispensing means by providing a blocking means such as an air bubble or a mechanical seal which, during the period between flushes, blocks the ports by which liquid flows into and out of the dispensing means. Depending on the type dispensing means used, and the materials used in constructing it, complete isolation of the concentrated solutions from the tank water may not always be possible since some small amount of solution may escape by capillary action, imperfect sealing of the inlet and outlet ports, etc. In any event, the greater the extent of isolation which can be obtained, the better.

Dispensers which completely or substantially completely isolate their contents from the tank water during the quiescent period between flushes are known to the art and are the preferred type for use in the present invention. Such dispensers are disclosed, for example, in U.S. Pat. No. 3,831,205, issued Aug. 27, 1974, to Foley; U.S. Pat. No. 3,341,074, issued Sept. 12, 1967, to Panutti; U.S. Pat. No. 4,036,407, issued July 19, 1977, to Slone; U.S. Pat. No. 4,171,564, issued Oct. 23, 1979, to Dirksing; U.S. Pat. No. 4,208,747, issued June 24, 1980, to Dirksing; and U.S. application Ser. No. 153,997, Choy, entitled PASSIVE DOSING DISPENSER EXHIBITING IMPROVED RESISTANCE TO CLOGGING, filed May 28, 1980. All of the foregoing patents and applications are incorporated herein by reference.

Preferably, the amount of santizing composition placed in the sanitizing composition dispensing means should be chosen so as to last at least as long as (i.e., through at least as may flushes as) the amount of dye-/activator composition in the dye/activator composition dispensing means. When the consumer no longer sees any color appear in the bowl when flushing the toilet, this indicates that it is time to replace the system (dye/activator and sanitizer). Conversely, if the consumer sees that color persists in the toilet bowl, this is also an indication that the supply of sanitizing agent has been exhausted and the system should be replaced. As indicated previously, it is less desirable to have a persistent color in the toilet bowl between flushes, and, therefore, it is preferable that the supply of sanitizer last for at least as long as the supply of dye/activator.

The dye plus activator and the sanitizing agents can be formulated into the form of liquid or solid compositions for use in the toilet sanitizing method herein. The form of the composition will depend upon the type of dispenser used. The most preferred dispensers are those which are designed to receive a solid composition. With this type of dispenser, water from the flush tank enters into the dispenser during the refill of the flush tank at the end of the flush. Water within the dispenser remains in contact with the solid composition between flushes, thereby forming a concentrated solution within the dispenser. When the toilet is flushed, a predetermined amount of the concentrated solution is discharged into the flush water as it flows from the tank to the bowl. Particularly preferred dispensers which are designed to receive a solid composition are those of the type disclosed in U.S. Pat. Nos. 4,171,546 and 4,208,747, supra. These dispensers also isolate the contents of the dispenser from the tank water during the quiescent period between flushes. In a preferred embodiment two dispensing means are constructed into a dual dispenser unit, one dispensing means containing the sanitizing agent composition and the other containing the dye/activator-salt composition. The two dispensing means in the dual dispenser unit can be of the same design or a different design from each other.

Accordingly, the present invention also encompasses an article of manufacture designed for placement below the high water line of the flush tank of a toilet comprising a flush tank and a bowl, said article comprising two dispensing means (i.e., dispensers), the first dispensing means containing a solid composition which is soluble in water and comprises a compound which provides hypochlorite ions in aqueous solution, and a second dispensing means containing a solid composition which is soluble in water and which contains an ortho-substituted triarylmethane dye (of the type hereinbefore set forth), a water-soluble source of bromide ion and a water-soluble source of ammonium ion, said first dispensing means and second dispensing means each having means for receiving water from the flush tank when said flush tank refills after a flush and for maintaining said received water in contact with the respective solid compositions in said first and second dispensing means during the quiescent period between flushes so as to form concentrated solutions of said compositions in said respective dispensing means between flushes, said first dispensing means and said second dispensing means each having means for releasing said concentrated solutions into the water in the flush tank when said water flows from the tank during flushing. When this article is placed in the flush tank of a toilet it is positioned in a manner such that the means for receiving water and the means for releasing concentrated solutions in both of the respective dispensing means are below the high water line of the flush tank. The first and second dispensing means function to produce a concentration of available chlorine from said hypochlorite of from about 2 ppm to about 30 ppm, a concentration of dye of from about 0.02 ppm to about 2 ppm, a ratio of available chlorine to dye of from about 2:1 to 150:1, a concentration of bromide ion of at least 0.1 ppm, a concentration of ammonium ion of at least 0.1 ppm and a pH of from about 6 to about 9.5 in the toilet bowl at the end of the flush. The color produced by said dye in the water in the toilet bowl disappears within about 40 minutes after the flush is completed. As indicated above, it is preferable that the respective dispensing means contain means for isolating the concentrated solutions of the respective compositions from the tank water during the quiescent periods between flushes.

The present invention will be illustrated by the following example.

EXAMPLE 1

This example illustrates the use of the present invention to provide a disappearing color signal in the automatic cleaning and sanitizing of the bowl of a flush toilet.

Sanitizer cakes for use in the present invention were prepared in the following manner.

A blend of HTH (70% calcium hypochlorite) from Olin Corp., Niagara Falls, New York; Form 2 (35% lithium hypochlorite) from Lithium Corporation of America, Bessemer City, North Carolina; sodium chloride; and Metzo Beads 2048 sodium metasilicate from Philadelphia Quartz Co. of Philadelphia, Pa., was dry mixed in a Day-Nauta mixer for 20 minutes and stamped into a 3.0 inch × 1.67 inch × 0.75 inch rectangular cake on a Stokes Model R-4 press at a force between 3.2 and 4.8 tons per square inch. The cake had the following composition and weighed approximately 100 grams.

| Ingredient | Wt. % |
| --- | --- |
| HTH | 56 |
| Form 2 | 15 |
| NaCl | 21.9 |
| Na metasilicate | 7.1 |
| Total | 100.0 |

Dye/activator-salt cakes for use in the present invention were prepared in the following manner.

A co-flaked mixture was first produced by mixing together Hostapur SAS 60 brand sodium paraffin sulfonate (approximately 84% active) from American Hoechst Co., Sommerville, N.J.; sodium chloride and a 40% aqueous solution of neutralized polyacrylamide resin (P-35 from Monsanto Co., St. Louis, Mo. in a steam heated mix tank with water to form a paste having a 60% solids content. The 40% aqueous solution of polyacrylamide resin was prepared by dissolving the resin in water and neutralizing to a pH (1% solution basis) of 5.0 to 5.5 with sulfuric acid. The paste of paraffin sulfonate, salt and resin was then heated to 150° F.± 10° F. and converted to flake form by drying to a moisture level of 1–2% on a drum dryer at 320° F.

The dried Hostapur/P-35/salt flakes were blended with ammonium bromide, FD&C Blue No. 1 dye and Hostapur SAS 60 flakes (made by drum drying Hostapur SAS 60, as received, to a moisture level of 1–2%), and the blend was dry-mixed in a double-arm Sigma-type mixer for 2–3 minutes. The perfume was then added, followed by 15 minutes of additional mixing. The resultant moist mixture was then plodded twice, once through a perforated plate and finally through a nozzle to form a log which was cut into cakes of approximately 65 grams having dimensions of approximately 3.34 inch×0.6 inch×1.94 inch. The cakes were dusted with talc. These cakes had the following composition:

| Ingredient | | Wt. % |
|---|---|---|
| Hostapur SAS 60 | | 68.73 |
| P-35 resin | Co-flaked | 11.30 |
| NaCl | Mixture | 1.00 |
| Hostapur SAS 60 flakes | | 3.44 |
| Ammonium bromide | | 5.10 |
| Pine Cone perfume | | 9.00 |
| FD&C Blue No. 1 | | 1.43 |
| | Total | 100.00 |

The above-described sanitizer cake and dye/activator-salt cake were sealed, respectively, into separate dispensers of a dual dispensing apparatus which was thermoformed from 0.022 inch thick polyvinyl chloride, and which is suitable for automatic, simultaneous dispensing of sanitizer solution and dye/activator-salt solution into a flushing toilet at each flush. Each of the dispensers in the dual dispensing apparatus was of a configuration generally similar to that described in FIG. 17 of U.S. Pat. No. 4,208,747, Dirksing, issued June 24, 1980. These separate dispensers (actually two separate dispensing means) of the dual dispensing apparatus produce concentrated solutions, respectively, of the sanitizer composition and the dye/activator-salt composition in water which enters the dispensers when the toilet tank is filling after a flush. The respective dispensing means serve to substantially isolate the concentrated solutions from each other and from the tank water during the period between flushes, although a very small amount of dye solution was found to migrate into the flush tank between flushes. The positioning of the respective dispensing means of the dual dispensing apparatus is such as to minimize mixing of the dispensed sanitizer and dye/activator-salt solutions during the flush until they have been diluted with flush water. The measuring cavity and inlet conduit of the sanitizer-containing portion of the dual dispensing apparatus is so sized that approximately 7 cubic centimeters of sanitizer-containing solution is dispensed with each flush cycle of the toilet.

The dye/activator-salt containing portion of the dual dispensing apparatus is so sized that approximately five cubic centimeters of dye/activator-salt containing solution is dispensed into the flush water as it leaves the tank during each flush cycle of the toilet.

The aforedescribed exemplary embodiment of a dual dispensing apparatus for carrying out the method of the present invention provides an excellent release of both the sanitizer-containing solution and the dye/activator-salt containing solution throughout the life of the unit.

An American Standard Cadet toilet comprising a flush tank and a bowl was equipped with this dispensing apparatus by mounting the apparatus in the tank with a mounting device of the type described in U.S. Ser. No. 060,088, Dirksing, filed July 23, 1979, incorporated by reference herein. One hour prior to mounting the apparatus in the toilet tank, water was introduced into the respective dispensers. The pH of the tank water was adjusted with either NaOH or HCl so as to give the desired pH in the toilet bowl after flushing. The temperature of the tank water was 70° F. The toilet was then flushed and the time elapsed from the beginning of the flush to the point at which the color disappeared from the bowl water was recorded. The available chlorine level in the bowl water was determined at the end of the flush, using Water Chex, a product of The Medical-Surgical Division of Parke, Davis & Co. Also, the pH of the bowl water at the end of the flush was determined with a pH meter. Results are set forth in Table 5.

TABLE 5

| Tank $H_2O$ pH | Bowl $H_2O$ pH | Bowl $H_2O$ Av.$Cl_2$ | Disappearance of Color in Bowl (Minutes) |
|---|---|---|---|
| 4.25 | 6.76 | 8 | 9 |
| 4.05 | 6.85 | 8 | 5 |
| 6.58 | 7.78 | 9 | 4 |
| 6.73 | 7.90 | 9 | 2¼ |
| 7.48 | 8.29 | 9 | 1½ |
| 6.97 | 8.30 | 4 | 1 |
| 9.93 | 9.09 | 8 | 5¾ |
| 10.11 | 9.19 | 9 | 5½ |

In the above experiment the sanitizer cake can be replaced with a sanitizer cake consisting of 80% HTH calcium hypochlorite, 9% Form 2 lithium hypochlorite and 11% sodium chloride, and similar color disappearance results will be obtained.

What is claimed is:
1. A composition of matter comprising:
(A) from about 0.2% to about 15% of a dye selected from the group consisting of water-soluble, ortho-substituted triarylmethane dyes which have in their structure the moiety.

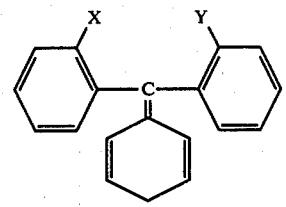

wherein X is selected from the group consisting of substituent groups other than hydrogen or methyl and Y is selected from the group consisting of X, hydrogen and methyl,
(B) an amount of a water-soluble bromide salt which provides from about 0.5% to about 18% by weight of bromide ion to said composition, and
(C) an amount of a water-soluble ammonium salt which provides from about 0.5% to about 11% by weight of ammonium ion to said composition.

2. The composition of claim 1 wherein the water-soluble bromide salt is present in an amount sufficient to provide from about 2% to about 8% by weight bromide ion to said composition and the water-soluble ammonium ion is present in an amount sufficient to provide from about 0.5% to about 1.5% ammonium ion to said composition.

3. The composition of claim 2 wherein the bromide salt is selected from the group consisting of alkali metal and ammonium bromides.

4. The composition of claim 3 wherein the ammonium bromide is the salt which provides both ammonium ions and bromide ions.

5. The composition of any one of claims 2, 3 and 4 wherein the X substituent on the dye is selected from the group consisting of halogen, sulfonate, carboxylate, phosphate, and hydroxyl, and the Y substituent is hydrogen.

6. The composition of claim 5 wherein the dye is selected from those having the Color Index designation 42053, 42090, 42045 and 42100.

7. The composition of claim 6 which additionally contains from about 5% to about 95% of a surfactant.

8. The composition of claim 7 wherein the dye is selected from the group consisting of those designated by Color Index Numbers 42090, 42053 and 42100.

* * * * *